United States Patent [19]
Fischer et al.

[11] Patent Number: 5,589,600
[45] Date of Patent: Dec. 31, 1996

[54] PREPARATION OF CYCLOHEXENE BY PARTIAL HYDROGENATION OF BENZENE

[75] Inventors: Rolf Fischer, Heidelberg; Roman Dostalek, Roemersberg; Laszlo Marosi, Ludwigshafen, all of Germany

[73] Assignee: BASF Aktiengesellschaft, Ludwigshafen, Germany

[21] Appl. No.: 450,981

[22] Filed: May 25, 1995

Related U.S. Application Data

[63] Continuation of Ser. No. 233,716, Apr. 26, 1994, abandoned, which is a continuation of Ser. No. 14,409, Feb. 5, 1993, abandoned.

[30] Foreign Application Priority Data

Feb. 5, 1992 [DE] Germany .................. 42 03 220.2

[51] Int. Cl.⁶ .................. C07C 5/10; C07C 5/11
[52] U.S. Cl. .................. 585/266; 585/269; 585/270; 585/271; 585/273; 585/275
[58] Field of Search .................. 585/266, 269, 585/270, 273, 274, 275, 276

[56] References Cited

U.S. PATENT DOCUMENTS

| | | | |
|---|---|---|---|
| 2,726,151 | 12/1955 | Kera | 75/5 |
| 3,899,543 | 8/1975 | Cosyns et al. | 585/258 |
| 3,912,787 | 10/1975 | Nowack et al. | 585/258 |
| 4,575,572 | 3/1986 | Ichihashi et al. | 585/266 |
| 4,734,536 | 3/1988 | Nagahara et al. | 585/269 |

FOREIGN PATENT DOCUMENTS 0055495  6/1984  European Pat. Off. .

OTHER PUBLICATIONS

*Gmelins Handbuch*, 1967, No. 57, pp. 604, 605, 612 and 613.
*Gmelins Handbuch*, 1970, No. 63, pp. 12 and 13.

*Primary Examiner*—Ponnathapura Achutamurthy
*Attorney, Agent, or Firm*—Keil & Weinkauf

[57] ABSTRACT

A process for the preparation of cyclohexene by partial hydrogenation of benzene with hydrogen in the presence of water and ruthenium catalysts modified with nickel, at elevated temperature in the liquid phase, wherein alloys of ruthenium with nickel are used as catalysts.

9 Claims, No Drawings

PREPARATION OF CYCLOHEXENE BY PARTIAL HYDROGENATION OF BENZENE

This application is a continuation of application Ser. No. 08/233,716, filed on Apr. 26, 1994, abandoned, which is a continuation of application Ser. No. 08/014,409, filed Feb. 5, 1993, abandoned.

This invention relates to a process for the preparation of cyclohexene by partial hydrogenation of benzene with hydrogen in the presence of ruthenium catalysts and water.

U.S. Pat. No. 4,197,415 discloses that cyclic olefins, e.g., cyclohexene are obtained by partial hydrogenation of aromatic hydrocarbons such as benzene in the presence of ruthenium catalysts. The ruthenium catalysts used in said reference are impregnated catalysts on supports such as mordenite and contain as promotors phosphates of Group IIb–VIIIb metals in the periodic table. Cyclohexene yields of 14 mol % are obtained at a selectivity of 29% using a ruthenium/nickel catalyst on a zeolitic support. It is desirable to improve on these values.

According to another process, described in U.S. Pat. No. 3,912,787, cyclohexene is obtained by hydrogenation of benzene in the presence of ruthenium catalysts, which contain manganese, cobalt, or nickel as promotors. The promotors can be fed to the reaction zone separately from the ruthenium. This leads to yields of up to 20 mol % of cyclohexene at a selectivity of 34% using a residence time of 62 min. In order to make the process suitable for large-scale production, it is necessary to improve on the results obtained.

According to another process, described in EP-A55,495, the preparation of cycloalkenes, e.g., cyclohexene is possible by partial hydrogenation, in the gas phase, of aromatic hydrocarbons such as benzene in the presence of a ruthenium catalyst with the concurrent use of steam. In addition to ruthenium, the catalyst can contain one or more metals or metal compounds selected from the group comprising iron, chromium, germanium, lead, zinc, nickel, and preferably sodium. Hydrogenation in the gas phase suffers from the drawback that large reaction chambers are necessary and, consequently, the space-time yield drops.

It is thus an object of the present invention to provide a process for the preparation of cyclohexene by partial hydrogenation of benzene in which high conversions of cyclohexene are achieved at high selectivities, short residence times are maintained, and a high space-time yield is achieved using a catalyst of improved stability.

This object is attained in a process for the preparation of cyclohexene by partial hydrogenation of benzene with hydrogen in the presence of water and ruthenium/nickel catalysts at elevated temperature under superatmospheric pressure in the liquid phase, wherein alloys of ruthenium with nickel are used as catalysts.

Our novel process has the advantage that it produces improved space-time yields, and higher conversions and increased selectivities toward cyclohexene are achieved. Another advantage of the novel process is that short residence times are made possible and the catalyst has an improved service life.

According to the invention, benzene is used as starting material, and this is partially hydrogenated with hydrogen to cyclohexene. Advantageously, the reaction is carried out at a temperature of from 20° to 300° C. Particularly good results have been obtained using a temperature of from 70° to 250° C., in particular from 100° to 200° C. Advantageously, a hydrogen partial pressure of from 1 to 200 bar and preferably from 10 to 100 bar is maintained. The hydrogenation is carried out in the liquid phase. That is to say, the temperature and pressure conditions must be matched in such a manner that a liquid phase is maintained.

An important feature of the invention is that the reaction is carried out in the presence of alloys of ruthenium with nickel as catalysts. Suitable ruthenium/nickel alloys have a nickel content of, say, from 0.01 to 50 wt %, based on the total ruthenium and nickel. Advantageously the nickel content is from 0.1 to 35 wt %. Particularly good results have been obtained using a nickel content of from 1 to 30 wt %.

Suitable ruthenium/nickel alloys can be obtained, for example, by intermixing, with vigorous stirring, a mixture of ruthenium compounds which are capable of being converted to ruthenium oxide, such as ruthenium(III) chloride or ruthenium(III) nitrate or ruthenium(III) chloropentamminochloride and nickel compounds which are capable of being converted to nickel oxide, such as nickel(II) chloride, nickel(II) sulfate, nickel(II) nitrate, or nickel acetate in the form of a, say, 1 to 8 wt % strength aqueous solution, with alkali lye, which advantageously has a concentration of from 10 to 40 wt %. It is advantageous to maintain a temperature of from 20° to 100° C. The precipitate obtained is then constantly stirred for a further 1 to 3 h at a temperature of from 60° to 100° C., in particular from 70° to 90° C., and the precipitate is then allowed to settle. The resulting precipitate is separated from the solution by decantation or filtration and then washed free from salts with slightly alkaline water, advantageously having a pH of from 10 to 11. It is then suspended in aqueous alkali lye having a pH of from 10 to 11 in a high-pressure vessel. Activation is then carried out under a hydrogen partial pressure of from 1 to 200 bar, preferably from 10 to 100 bar and more preferably from 20 to 80 bar and at a temperature of from 50° to 300° C., advantageously from 100° to 270° C. and in particular from 120° to 250° C., with stirring, for a period of from 4 to 8 h, in particular for a period of from 5 to 7 h. The resulting catalyst powder is separated from the caustic soda solution, e.g., by decantation and then washed to neutrality with water under a protective blanket of, say, nitrogen or argon and then dried under reduced pressure at an elevated temperature, e.g., from 40° to 70° C.

Ruthenium/nickel alloys are advantageous whose space lattice constants for the a-axis are of from 0.2610 to 0.2705 nm and for the c-axis are from 0.4200 to 0.4280 nm. These values show that that the blends are not simple mixtures of elementary ruthenium with nickel, but are genuine alloys.

The X-ray diffraction patterns are produced using a Siemens Diffractometer D-500 equipped with a secondary monochromatic filter and scintillation counter. Use is made of copper $K\alpha$ radiation (40 kV, 30 mA). In order to determine the exact positions of the lines zinc oxide is added to the samples to provide an internal standard and the space-lattice constants $a_0$ and $c_0$ of the catalyst specimen are calculated from the position of the reflexes (100) and (102).

The ruthenium/nickel alloy is generally employed without the use of a catalyst support. However, it may be advantageous to use supports such as aluminum oxide, silicon dioxide, zirconium dioxide, lanthanum oxide, activated charcoal, zinc oxide and titanium dioxide.

Advantageously, there is used from 0.001 to 50 wt % of ruthenium/nickel alloy, based on the benzene used. Particularly good results have been obtained using amounts of from 0.05 to 10 wt %, in particular from 0.1 to 2 wt %.

The reaction is carried out in the presence of water. The amount of water employed, based on the total amount of liquid, should preferably be from 5 to 90 wt %. Advantageously the aqueous phase contains one or more dissolved cations of Group II to VIII transition metals in the periodic table such as chromium, manganese, iron, cobalt, zinc, or ammonium in the form of their chlorides, nitrates, acetates, phosphates, or sulfates. Cobalt and zinc sulfates and especially zinc sulfate are particularly preferred. The pH of this salt solution is advantageously neutral to slightly acid, e.g., its pH is from 3 to 7. The amount of metal salt, based on the aqueous phase, is advantageously from 0.1 wt % up to saturation point.

It has also been found to be beneficial to add to the reaction mixture at least one of the metal oxides selected from the group consisting of aluminum oxide, silicon dioxide, zirconium dioxide, titanium dioxide, hafnium dioxide, chromium trioxide, and zinc oxide. Preferably the amount of metal oxide added is from $5 \cdot 10^{-4}$ to 20 wt %, based on the amount of water used.

The hydrogenation can be carried out continuously or batchwise, e.g., in suspension or over a fixed bed catalyst.

The cyclohexene obtainable by means of the process of the invention is suitable for the preparation of cyclohexanol, an important starting material for the preparation of fiber precursors.

The process of the invention is illustrated below with reference to the following examples:

EXAMPLE 1

15 g of ruthenium(III) chloride·3H$_2$O and 5.6 g of nickel(II) chloride·6H$_2$O are dissolved in 700 mL water and, with vigorous stirring, quickly intermixed with 100 mL of a 20% strength caustic soda solution. Stirring of the precipitate obtained is continued for approximately another 2 h at 80° C. and it is then allowed to settle over a period of 10 h, after which the supernatant solution is removed by decantation and the precipitate is washed to neutrality with a total of 1000 mL of slightly alkaline water (pH 11). Following transfer to a stirred autoclave having a capacity of 1 L and lined with Teflon together with 500 mL of very dilute caustic soda solution (pH 10–11) under 50 bar of hydrogen, the mixture is stirred at 170° C. for a period of six hours. The resulting catalyst powder is washed to neutrality with water under a blanket of argon and then dried in vacuo at 60° C. There are obtained 7.5 g of catalyst alloy having a nickel content of 20 wt %.

0.3 g of this catalyst alloy, 9.6 g of ZnSO$_4$7H$_2$O, 1.2 g of ZrO$_2$, 95 mL of water and 45 mL of benzene are heated to 150° C. in an autoclave having a capacity of 30mL, with vigorous stirring. On reaching this temperature, the autoclave is pressurized to a pressure of 50 bar of hydrogen and the mixture is stirred over a predetermined period, after which the organic phase is separated and subjected to gas-chromatographic analysis. The results are listed in Table 1 below.

EXAMPLE 2

The benzene hydrogenation was carried out as in Example 1 using a catalyst, whose nickel content was adjusted to 24.3 wt % following the instructions given in Example 1, but using a correspondingly larger amount of NiCl$_2$·6H$_2$O.

EXAMPLE 3

The benzene hydrogenation was carried out as in Example 2, but without the addition of ZnSO$_4$.

EXAMPLE 4

The benzene hydrogenation was carried out as in Example 2, but using 9.6 g of CoSO$_4$ instead of 9.6 g of ZnSO$_4$.

EXAMPLE 5

The benzene hydrogenation was carried out as in Example 1 using a catalyst which contained 17 wt % of nickel, at a reaction temperature of 170° C.

EXAMPLE 6

The benzene hydrogenation was carried out as in Example 1 using a catalyst which contained 16 wt % of nickel.

EXAMPLE 7

The benzene hydrogenation was carried out as in Example 1 using a catalyst which contained 15 wt % of nickel.

EXAMPLES 8 AND 9

The benzene hydrogenation was carried out as in Example 5, but using 9.6 g of ZnCl$_2$, and 9.6 g of CoSO$_4$, respectively, instead of ZnSO$_4$.

EXAMPLES 10 AND 11

(Comparative Examples)

The benzene hydrogenation was carried out as in Example 1 but using mixtures of finely divided ruthenium and nickel powder as hydrogenation catalysts. The results shown in Table 1 demonstrate that the use of alloys of these two elements provides distinctly higher cyclohexene yields and selectivities.

The results obtained are listed in the following table.

TABLE

Batch experiments using various suspended Ru/Ni catalysts

| Example No. | Nickel content (wt %) | Residence Time (?) | Metal Salt | Metal oxide | Water/Benzene ratio | Yield CHE (mol %) | Selectivity CHE (mol %) |
|---|---|---|---|---|---|---|---|
| 1 | 20 | 15 | 9.6 g of ZnSO$_4$ | 1.2 g of ZrO$_2$ | 95 mL/45 mL | 16.0 | 76 |
|  | 20 | 30 | 9.6 g of ZnSO$_4$ | 1.2 g of ZrO$_2$ | 95 mL/45 mL | 29.0 | 66 |
|  | 20 | 45 | 9.6 g of ZnSO$_4$ | 1.2 g of ZrO$_2$ | 95 mL/45 mL | 33.0 | 61 |
| 2 | 24.3 | 15 | 9.6 g of ZnSO$_4$ | 1.2 g of ZrO$_2$ | 95 mL/45 mL | 15.0 | 72 |
| 3 | 24.3 | 15 | none | 1.2 g of ZrO$_2$ | 95 mL/45 mL | 19.0 | 18 |
| 4 | 24.3 | 15 | 9.6 g of CoSO$_4$ | 1.2 g of ZrO$_2$ | 95 mL/45 mL | 20.0 | 50 |
| 5 | 17 | 30 | 9.6 g of ZnSO$_4$ | 1.2 g of ZrO$_2$ | 95 mL/45 mL | 31.0 | 71 |
| 6 | 16 | 30 | 9.6 g of ZnSO$_4$ | 1.2 g of ZrO$_2$ | 95 mL/45 mL | 40.0 | 58 |
| 7 | 15 | 15 | 9.6 g of ZnSO$_4$ | 1.2 g of ZrO$_2$ | 95 mL/45 mL | 23.0 | 65 |
| 8 | 15 | 15 | 9.6 g of ZnCl$_2$ | 1.2 g of ZrO$_2$ | 95 mL/45 mL | 21.0 | 30 |
| 9 | 15 | 15 | 9.6 g of CoSO$_4$ | 1.2 g of ZrO$_2$ | 95 mL/45 mL | 15.0 | 62 |

TABLE-continued

| | Batch experiments using various suspended Ru/Ni catalysts | | | | | | |
|---|---|---|---|---|---|---|---|
| Example No. | Nickel content (wt %) | Residence Time (?) | Metal Salt | Metal oxide | Water/Benzene ratio | Yield CHE (mol %) | Selectivity CHE (mol %) |
| 10 comp. | elem. Ni (60 mg)+ elem. Ru (24 mg) | 15 | 9.6 g of $ZnSO_4$ | 1.2 g of $ZrO_2$ | 95 mL/45 mL | 12.0 | 33 |
| 11 comp. | elem. Ni (150 mg)+ elem. Ru (150 mg) | 15 | 9.6 g of $ZnSO_4$ | 1.2 g of $ZrO_2$ | 95 mL/45 mL | 0.2 | 21 |

We claim:

1. A process for the preparation of cyclohexene by the partial hydrogenation of benzene with hydrogen which comprises: carrying out the partial hydrogenation reaction at elevated temperatures of from about 20° to about 300° C. in an aqueous and liquid phase in the presence of a ruthenium/nickel alloy catalyst having a space lattice constant for the a-axis of from 0.2610 to 0.2705 nm and for the c-axis of from 0.4200 to 0.4280 nm, wherein the aqueous phase contains one or more dissolved cations of Group II to VIII transition metals of the periodic table as promoters.

2. A process as defined in claim 1, wherein the ruthenium/nickel alloy has a nickel content of from 1 to 30 wt %.

3. A process as defined in claim 1, wherein the amount of water, based on the total amount of liquid, is from 5 to 90 wt %.

4. A process as defined in claim 1, wherein the aqueous phase is neutral to slightly acid.

5. A process as defined in claim 1, wherein zinc sulfate and/or cobalt sulfate are used as promotors.

6. A process as defined in claim 1, wherein the partial hydrogenation reaction is carried out in the presence of at least one metal oxide selected from the group consisting of aluminum oxide, silicon dioxide, zirconium dioxide, titanium dioxide, hafnium dioxide, chromium trioxide and zinc oxide.

7. A process as defined in claim 1, wherein from $5 \cdot 10^{-4}$ to 20 wt % of metal oxides is added, to the reaction mixture based on the weight of water.

8. A process as defined in claim 1, wherein the reaction is carried out at a temperature of from 100° to 200° C.

9. A process as defined in claim 1, wherein the hydrogen partial pressure is from 10 to 100 mbar.

* * * * *

UNITED STATES PATENT AND TRADEMARK OFFICE
CERTIFICATE OF CORRECTION

PATENT NO.: 5,589,600

DATED: December 31, 1996

INVENTOR(S): FISCHER et al.

It is certified that error appears in the above-identified patent and that said Letters Patent is hereby corrected as shown below:

Column 5, claim 1, line 5, after "liquid phase" insert --reaction mixture--.

Signed and Sealed this

Twenty-fifth Day of February, 1997

Attest:

BRUCE LEHMAN

*Attesting Officer*   *Commissioner of Patents and Trademarks*